United States Patent
Weber (10) Patent No.: US 7,271,898 B2
(45) Date of Patent: Sep. 18, 2007

(54) METHOD AND SYSTEM FOR REMOTE SENSING OF OPTICAL INSTRUMENTS AND ANALYSIS THEREOF

(75) Inventor: Jonathan L. Weber, Nashua, NH (US)

(73) Assignees: BAE Systems Information, Nashua, NH (US); Electronic Systems Integration Inc., Nashua, NH (US)

(*) Notice: Subject to any disclaimer, the term of this patent is extended or adjusted under 35 U.S.C. 154(b) by 213 days.

(21) Appl. No.: 11/040,754

(22) Filed: Jan. 19, 2005

(65) Prior Publication Data

US 2006/0158646 A1 Jul. 20, 2006

(51) Int. Cl.
*G01J 3/30* (2006.01)

(52) U.S. Cl. .................................... 356/318; 356/317

(58) Field of Classification Search ........ 356/317–320, 356/213; 250/458.1, 459.1, 461.1, 339.01, 250/339.11
See application file for complete search history.

(56) References Cited

U.S. PATENT DOCUMENTS

| | | | | |
|---|---|---|---|---|
| 3,215,842 A * | 11/1965 | Thomas | ...................... | 398/170 |
| 4,247,770 A * | 1/1981 | Welch | ......................... | 250/253 |
| 5,446,538 A * | 8/1995 | Noll | ............................ | 356/318 |
| 5,528,364 A * | 6/1996 | Koike | ......................... | 356/334 |
| 5,537,206 A * | 7/1996 | Akiyoshi et al. | ............ | 356/315 |
| 5,541,413 A * | 7/1996 | Pearson et al. | ......... | 250/339.11 |
| 5,608,519 A * | 3/1997 | Gourley et al. | .............. | 356/318 |
| 5,608,520 A * | 3/1997 | Fleming | ...................... | 356/318 |
| 5,751,416 A * | 5/1998 | Singh et al. | ................. | 356/311 |
| 5,847,825 A | 12/1998 | Alexander | | |
| 6,008,896 A * | 12/1999 | Sabsabi et al. | .............. | 356/318 |
| 6,603,134 B1 | 8/2003 | Wild et al. | ................... | 250/526 |
| 6,762,835 B2 * | 7/2004 | Zhang et al. | ................ | 356/318 |
| 6,762,836 B2 * | 7/2004 | Benicewicz et al. | ......... | 356/318 |
| 6,853,452 B1 * | 2/2005 | Laufer | ......................... | 356/436 |
| 6,909,505 B2 * | 6/2005 | Lucas et al. | ................. | 356/318 |
| 7,016,035 B2 * | 3/2006 | Wu et al. | ..................... | 356/318 |

OTHER PUBLICATIONS

PCT International Search Report dated Nov. 27, 2006 of International Application No. PCT/US2005/046051 filed Dec. 20, 2005.

* cited by examiner

*Primary Examiner*—Sang H. Nguyen
(74) *Attorney, Agent, or Firm*—Hayes Soloway P.C.

(57) ABSTRACT

A sensor is provided for analyzing an object at a focal point of a lens. The sensor includes a focused radiant energy source directed at the lens. The focused radiant energy source transmits a first beam of energy to the lens, vaporizing a portion of the object at the focal point of the lens. A second beam of energy is emitted from the vaporization of the object. A spectrometer is positioned to receive the second beam of energy emitted from the object. The second beam of energy is at least partially transmitted anti-parallel to the first beam of energy.

15 Claims, 7 Drawing Sheets

METHOD AND SYSTEM FOR REMOTE SENSING OF OPTICAL INSTRUMENTS AND ANALYSIS THEREOF

FIELD OF THE INVENTION

The present invention relates to optics. More specifically, the present invention relates to optical sensors.

BACKGROUND OF THE INVENTION

With advancements in the field of optics, use of retro-reflectors has become more common. A retro-reflector is defined as a reflector wherein incident rays or radiant energy and reflected rays are parallel for any angle of incidence within the field-of-view. A characteristic of a retro-reflector is that the energy impinging thereon is reflected in a very narrow beam, herein referred to as the retro-reflected beam. This phenomenon was termed retro-reflection. Retro-reflectors are discussed, for instance, in U.S. Pat. No. 6,603,134, which issued Aug. 5, 2003. Those inventors made the discovery that any type of focusing device, in combination with a surface exhibiting any degree of reflectivity and positioned near the focal plane of the device, acts as a retro-reflector.

Figure 1:
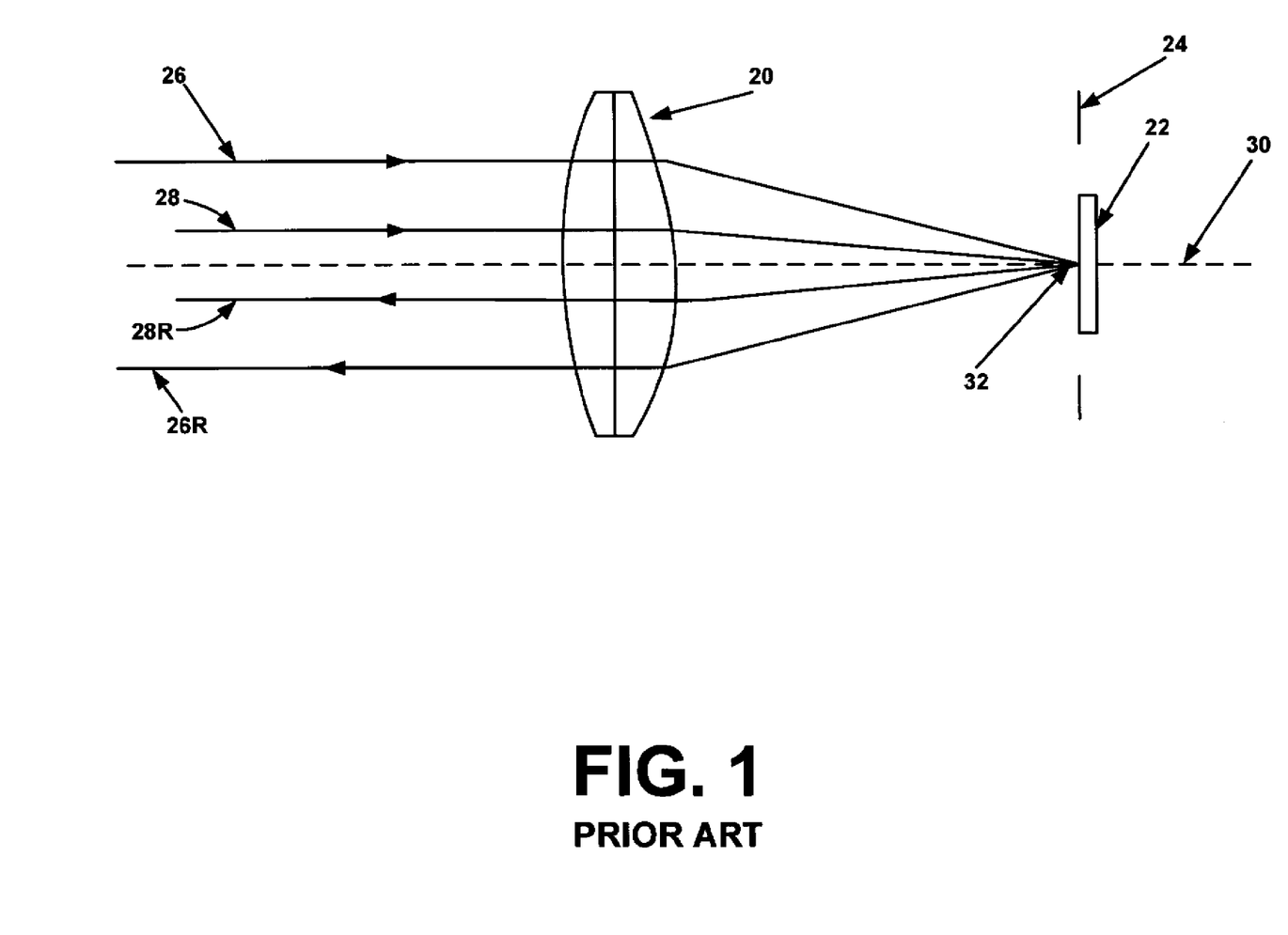
FIG. 1 is a prior art diagram showing a retro-reflection system containing a lens and a reflective surface positioned in a focal plane of the lens.

FIG. 1 is a prior art diagram showing a retro-reflection system containing a lens 20 and a reflective surface 22 positioned in a focal plane 24 of the lens 20. Rays of radiation 26, 28 are directed toward the system, and more particularly toward the lens 20, from a radiation source (not shown). The incident rays in the present illustration are parallel to the optical axis 30 of the lens 20. It should be noted that for the purpose of clarity, the incident rays are shown as being confined to the top half of the lens 20. The incident rays 26 and 28 are refracted by the lens 20 and focused at the focal point 32 of the lens 20, which focal point lies on the reflective surface 22. The rays 26, 28 are then reflected by the reflective surface 22 so that the angle of reflection equals the angle of incidence, and are returned approximately to the lower half of the lens 20 where they are again refracted and emerge therefrom as retro-reflected rays 26R, 28R. The rays 26R and 28R are returned to the radiation source parallel to the incident rays 26, 28 thereof. However, as shown in the drawing, the relative positions of the rays 26, 28 are inverted so that the image returned to the radiation source is also inverted. It should be noted that the lens 20 and reflective surface 22 could, for instance, be elements of an optical device, such as a camera, or an eye of a person or animal.

FIG. 1 shows the basic retro-reflection characteristic of focused lens systems. Rays 26 and 28 enter the aperture, are focused to a point, and then re-projected virtually anti-parallel as shown by rays 26R and 28R. The usual method for calculating the return intensity is to take it as the product of the flux density of the probe radiation and a quantity called the optical augmentation cross section. This is proportional to the aperture area multiplied by the two way transmission and the optical augmentation optical gain. This is defined as the ratio of the aperture area to the image spot area multiplied by the backscatter factor and has dimensions square meters per steradians. Because the focused spot is much smaller than the aperture, this optical gain factor can be very large. This results in a much larger return than would come from the more typical scatterer. The gain in this process is due to the backscatter being narrowly directed, i.e. anti-parallel, rather than diffusively scattered over a hemisphere.

While FIG. 1 depicts the lens 20 positioned at a right angle to the rays 26, 28, U.S. Pat. No. 6,603,134 teaches that retro-reflection does not require an orthogonal relationship between the lens 20 and the rays 26, 28.

Figure 2:
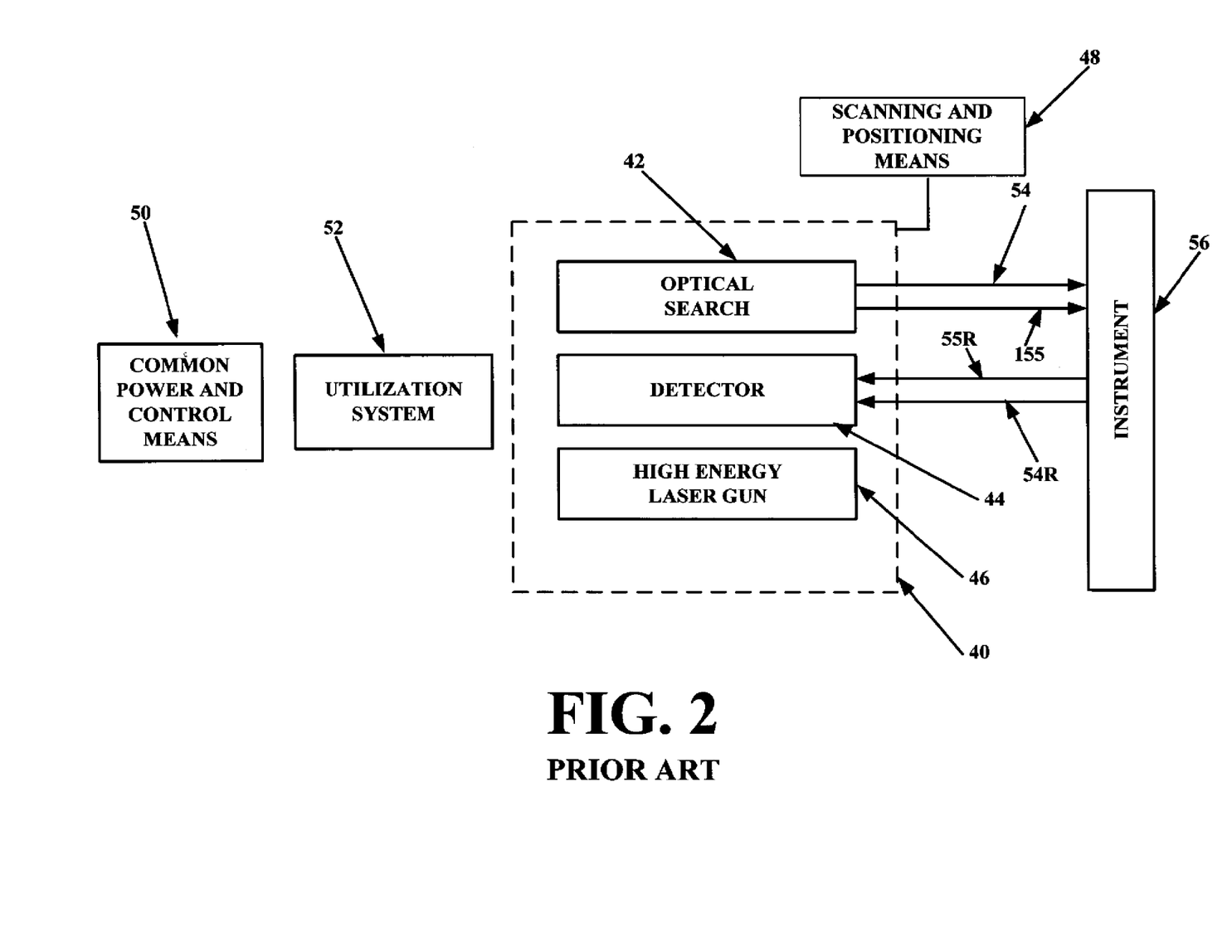
FIG. 2 is a prior art diagram depicting a search system for scanning an area to detect the presence of optical instruments by using retro-reflective properties.

One application for the retro-reflectors is to search for cameras, otherwise referred to as optical instruments herein, in an area. FIG. 2 depicts a search system 38 for scanning an area to detect the presence of optical instruments by using retro-reflective properties. The search system 38 includes a scanner 40, including an optical searching device 42, such as a source of infrared light, a detector 44, and a laser 46. The scanner 40 is controlled by a scanning and positioning device 48, which includes a servo motor (not shown). The scanning and positioning device 48 is powered by a power and control device 50, which also supplies power to the scanner 40, and a utilization system 52.

In the operation of the system 38, the scanner 40 is caused to scan a preselected area by means of the scanning and positioning device 48, the scanning and positioning device 48 being programmed by the utilization system 52. The optical searching device 42 emits rays 54, 55. When these rays 54, 55 impinge on an optical instrument 56 exhibiting retro-reflective characteristics, the rays 54, 55 are retro-reflected as retro-reflected rays 54R, 55R and detected by the detector 44. The detector output is then fed to the utilization system 52. The utilization system 52 may be programmed to merely track the optical instrument 56, in which case, the detector output would be fed to the scanning and positioning device 48 and then to the scanner 40, causing the scanning and positioning device 48 to track the optical instrument 56. However, if it is desired to neutralize the optical instrument 56, the utilization system 52 will feed a signal to the laser 46 causing the laser 46 to direct a high intensity laser beam at the optical instrument 56.

This type of search system 38 can have false alarms due to natural and artificial retro-reflections. Natural retro-reflections can occur from sand or other naturally occurring open cube corners. Examples of artificial retro-reflectors include corner cubes such as those used in surveying, rear reflectors on automobiles and bicycles, as well as retro-reflective coated items, such as sportswear and traffic signs.

Thus, a heretofore unaddressed need exists in the industry to address the aforementioned deficiencies and inadequacies.

SUMMARY OF THE INVENTION

Embodiments of the present invention provide a system and method for remote sensing of optical instruments and analysis thereof. Briefly described in architecture, one embodiment of the system, among others, can be implemented as follows. A sensor is provided for analyzing an object at a focal point of a lens. The sensor includes a focused radiant energy source directed at the lens. The focused radiant energy source emits a first beam, which vaporizes a portion of the object at the focal point of the lens. A spectrometer is positioned to receive a second beam of energy emitted from the vaporization of the portion of the object. A path of the second beam of energy is at least partially anti-parallel to a path of the first beam.

In another aspect, the invention features a method for chemical analysis of a remotely located object at a focal point of a lens. The method includes the steps of: transmitting a first radiant energy beam at the lens and, therethrough, the object vaporizing a portion of the object; and receiving a second beam of energy, emitted from the vaporization of the object, at a spectrometer, wherein the second beam of energy is at least partially transmitted anti-parallel to the first radiant energy beam.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 3:
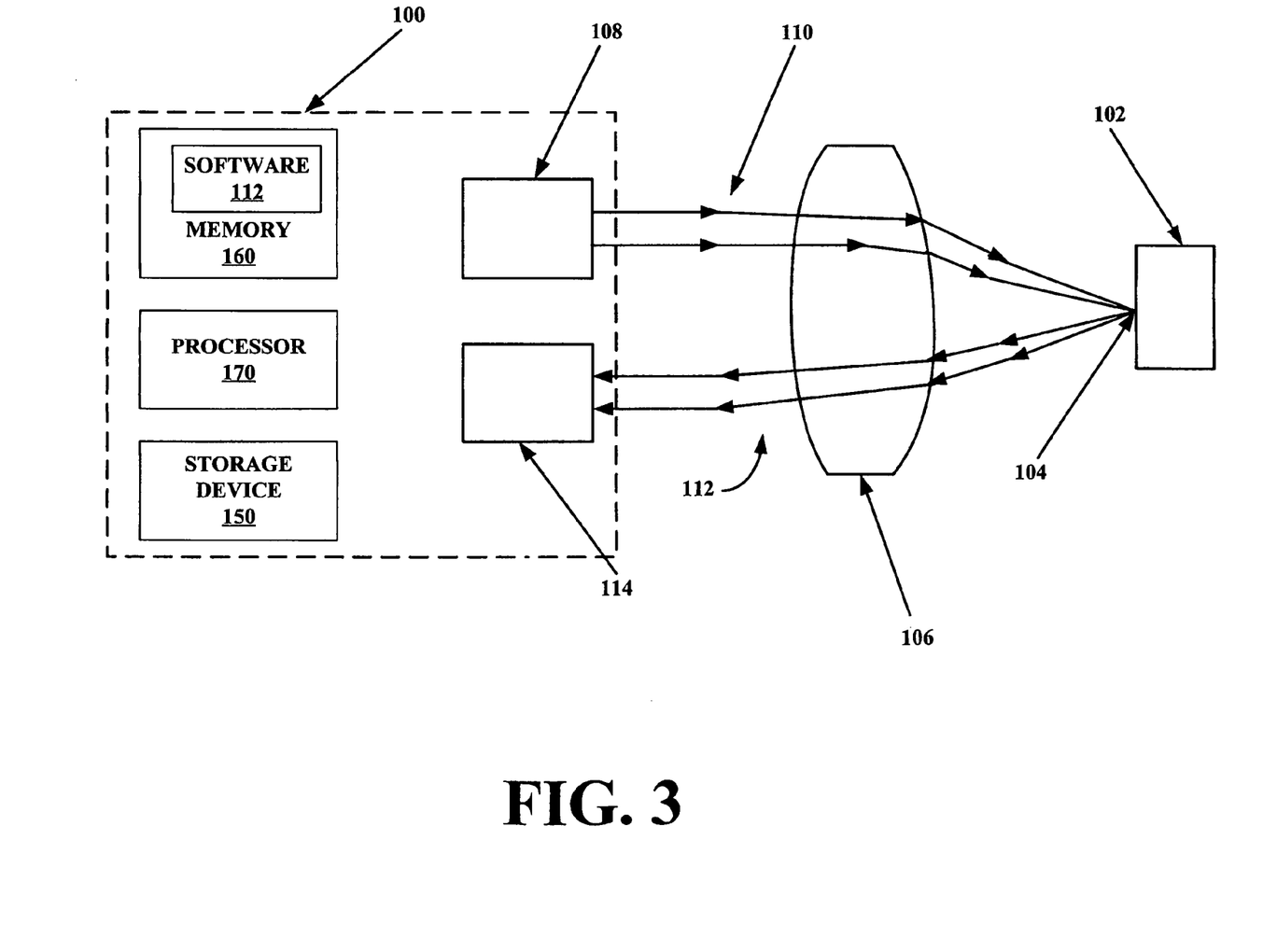
FIG. 3 is a block diagram of a sensor, in accordance with a first exemplary embodiment of the invention.

FIG. 3 is a block diagram of a sensor 100, in accordance with a first exemplary embodiment of the invention. The sensor 100 provides analysis of an object 102 at a focal point 104 of a lens 106. The sensor 100 includes a focused radiant energy source 108 directed at the lens 106. The focused radiant energy source 108 is capable of transmitting a first radiant energy beam 110 to the lens 106 and, therethrough, to the object 102. The first radiant energy beam 110 may be of sufficient intensity at the focal point 104 of the lens 106 to vaporize at least a portion of the object 102. Upon vaporization, a second beam 112 of energy is emitted from the vaporization of object 102 and through the lens 106. A spectrometer 114 is positioned to receive the second beam 112 of energy refracted from the lens 106 and the object 102. A path of the second beam 112 of energy is at least partially anti-parallel to a path of the first radiant energy beam 110.

The sensor is capable of providing information helpful in identifying the object 102. The first radiant energy beam 110 is focused by the lens 106 into a very narrow beam at the focal point 104. The focused first radiant energy beam 110 vaporizes a relatively small portion of the object 102. As taught in the field of atomic emission spectroscopy, when a laser vaporizes atoms, it raises those atoms to higher energy levels. The atoms decay back to lower energy levels by emitting energy. Quantitative measurements of these energy emissions can be used to determine analyte concentration and, ultimately, retrieve chemical information regarding the vaporized object. This chemical information can then be used to determine what material was vaporized.

While the first radiant energy beam 110 is intended to vaporize the object 102 at the focal point 104, very little vaporization is required for analysis of the object 102. In the case of the lens 106 and object 102 being parts of a camera, the first radiant energy beam 110 can be manipulated to vaporize a small portion of the camera without doing significant damage to a single pixel.

The first radiant energy beam 110 impacts the object 102 at the focal point 104 and vaporizes a portion of the object 102. The emitted energy from the decaying vaporized atoms forms the second beam 112, which traverses a path substantially similar to a path that would be followed if the first radiant energy beam 110 were simply retro-reflected. The second beam 112 is transmitted from the object 102 through the lens 106 where the second beam 112 is directed back toward the sensor 100. More precisely, the second beam 112 radiates along a path anti-parallel to a path of the first radiant energy beam 110 and toward the spectrometer 114. The spectrometer 114 is positioned to receive the second beam 112 and is capable of analyzing the second beam 112 to identify the emissions from the decaying vaporized atoms and can be used to determine an elemental content at the focal point 106, primarily composition the object 102.

To determine what material has been vaporized, the sensor 100 may also contain a storage device 150 a memory 160, having software 162 stored therein, and a processor 170. The storage device 150 has stored therein names of different materials and their emission identities. Therefore, in accordance with the software 162 located within the memory 160, the memory 160 instructs the processor 170 to search for the emission identity derived by the spectrometer 114, within the storage device 150. The result of this search is the material that was vaporized by the first radiant energy beam 110.

In accordance with an alternative embodiment of the invention, cameras having different material properties are also stored within the storage device 150. Therefore, by determining the material that was vaporized within the storage device 150, possible associated cameras may be identified so that other actions may be performed accordingly.

It should be noted that the second and third embodiment sensors, as described herein may also contain a memory, software, processor, and a storage device and function similarly to determine the vaporized material.

The first radiant energy beam 110 may be any of a variety of energy types, although it may be more efficient to use radiation in or near an operating band of the target sensor, for reasons discussed herein. The first radiant energy beam 110 may comprise light energy, microwave energy, acoustical energy, X-ray energy, heat energy, and/or any other energy types that are part of the energy spectrum and that are capable of vaporizing a portion of the object 102, whilst exhibiting the ability to return the anti-parallel second beam 112. In situations where it is desirable to conceal the sensor 100, an energy type may be selected that is not visible to the naked eye. One type of energy, as an example, that may be desirable is infrared light and, more particularly, infrared light in an eyesafe band. Improperly regulated, the first radiant energy beam 110 or second beam 112 may be capable of blinding a person or animal, if an eye is struck by either beam 110, 112. Infrared light in the eyesafe band, approximated by some as being above 1.54 microns in wavelength, is at least partially absorbed in the eye, before it can be focused on the retina, eliminating the lowest energy eye damage modality, retinal burn.

The spectrometer 114 may be implemented with or without a slit. Classical slitted spectrometers include an entrance slit, a collimating optic, usually a mirror, a disperser, such as a diffraction grating or prism, and a focusing optic, also usually a mirror. Diffraction gratings have the benefits of providing a linear wavelength dispersion at the focus and are fairly efficient in the design bands. They have the disadvantage that they have order ambiguity (i.e., second order short wavelength radiation can be imaged at the same place as first order at twice the wavelength. Slitted spectrometers are inconvenient for operation in the thermal infrared region because they almost always have to be cooled. Thermal imagers have become very efficient at avoiding internally generated radiation by placement of the entrance or exit pupils. Slitted spectrometers do not allow this freedom, so the usual approach to suppression of internal interfering radiation is to cool the interiors.

Slitless spectrometers include a camera with a dispersing element incorporated into the objective lens. Slitless spectrometers were used extensively for astronomical star field mapping where the separated stars in the sky eliminated the confusion caused by the overlaps that would confuse a spectrum of an extended or complex object. The dispersing element can be either a prism or a transmission grating. Since the probe beam will be applied to a very narrow field of view with a small number of tracking sensors, each producing a point-like return, the spectrum returned is readily interpreted.

Figure 4:
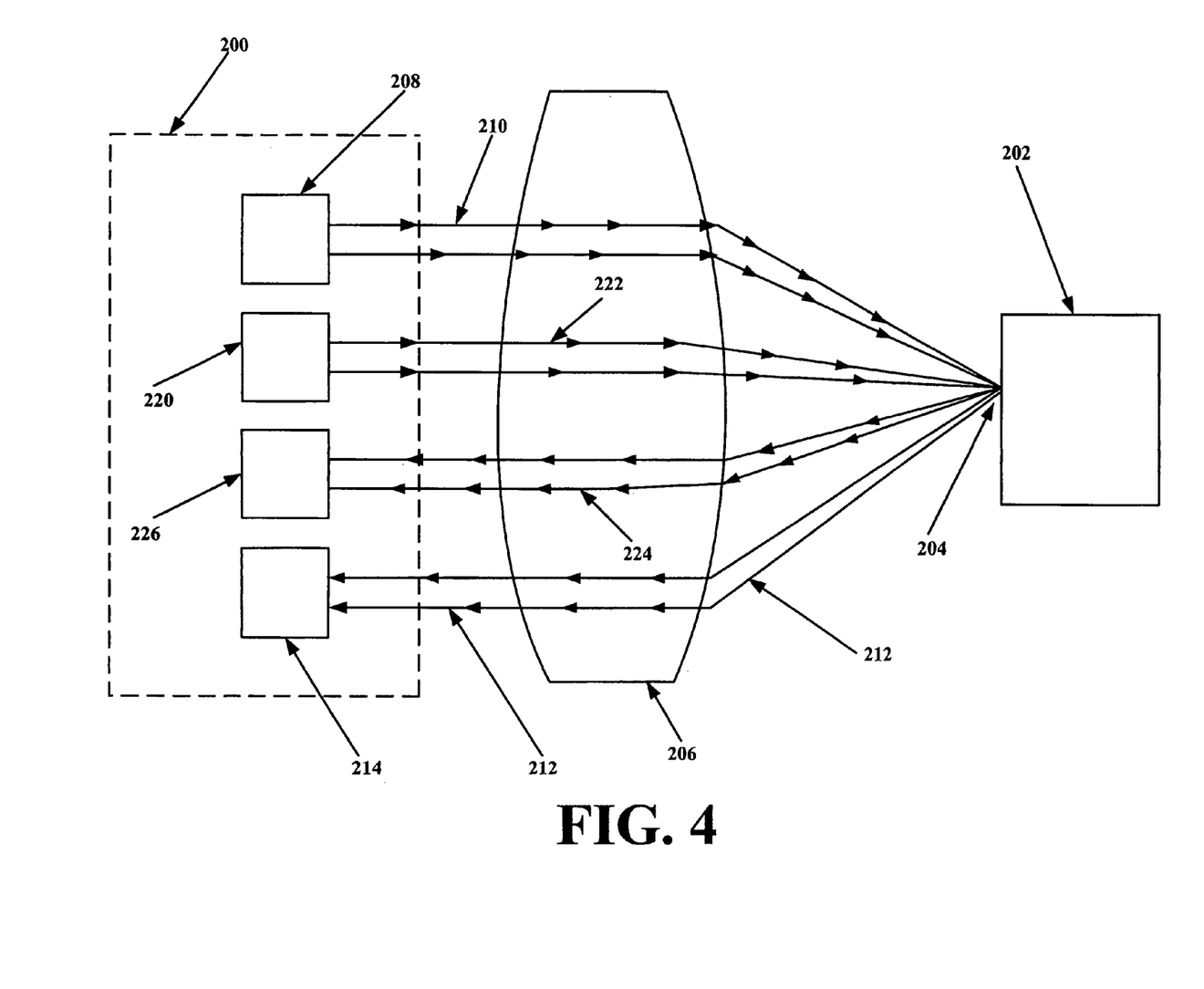
FIG. 4 is a block diagram of a sensor, in accordance with a second exemplary embodiment of the invention.

FIG. 4 is a block diagram of a sensor 200 in accordance with a second exemplary embodiment of the invention. The sensor 200 provides analysis of an object 202 at a focal point 204 of a lens 206. The sensor 200 includes a focused radiant energy source 208 directed at the lens 206. The focused radiant energy source 208 is capable of transmitting a first beam 210 of energy to the lens 206 and, therethrough, to the object 202. The first radiant energy beam 210 may be of sufficient intensity at the focal point 204 of the lens 206 to vaporize at least a portion of the object 202. Upon vaporization, a second beam 212 of energy is emitted from the object 202 and refracted through the lens 206. A spectrometer 214 is positioned to receive the second beam 212 of energy refracted from the lens 206. A path of the second beam 212 of energy is at least partially anti-parallel to a path of the first beam 210 of energy.

The second exemplary embodiment of the sensor 200 further includes a radiant energy search beam source 220. The radiant energy search beam source 220 operates under similar principles as the focused radiant energy source 208, with the exception that a first search beam 222 emitted from the radiant energy search beam source 220 is not of sufficient intensity to vaporize the object 202 even after focused by the lens 206. The first search beam 222, depending on the characteristics of the object 202, is retro-reflected back toward the lens 206 as a second search beam 224. The second search beam 224 is transmitted back through the lens 206 after which the second search beam 224 is directed back toward the sensor 200. More precisely, the second search beam 224 radiates along a path anti-parallel to a path of the first search beam 222 and toward a detector 226. The detector 226 detects whether the retro-reflected second search beam 224 is in excess of a preselected radiant flux density level, which would indicate the presence of an optical device, for example, but not limited to, a tracking optical device.

In operation, the radiant energy search beam source 220 and detector 226 may be used to scan an area for optical devices, and the focused radiant energy source 208 and spectrometer 214 may be used to analyze located optical devices.

As shown in FIG. 4, the radiant energy search beam source 220 and the focused radiant energy source 208 are separate devices in the second embodiment. A third exemplary embodiment may be provided in which the radiant energy search beam source 220 and the focused radiant energy source 208 are the same device.

Figure 5:
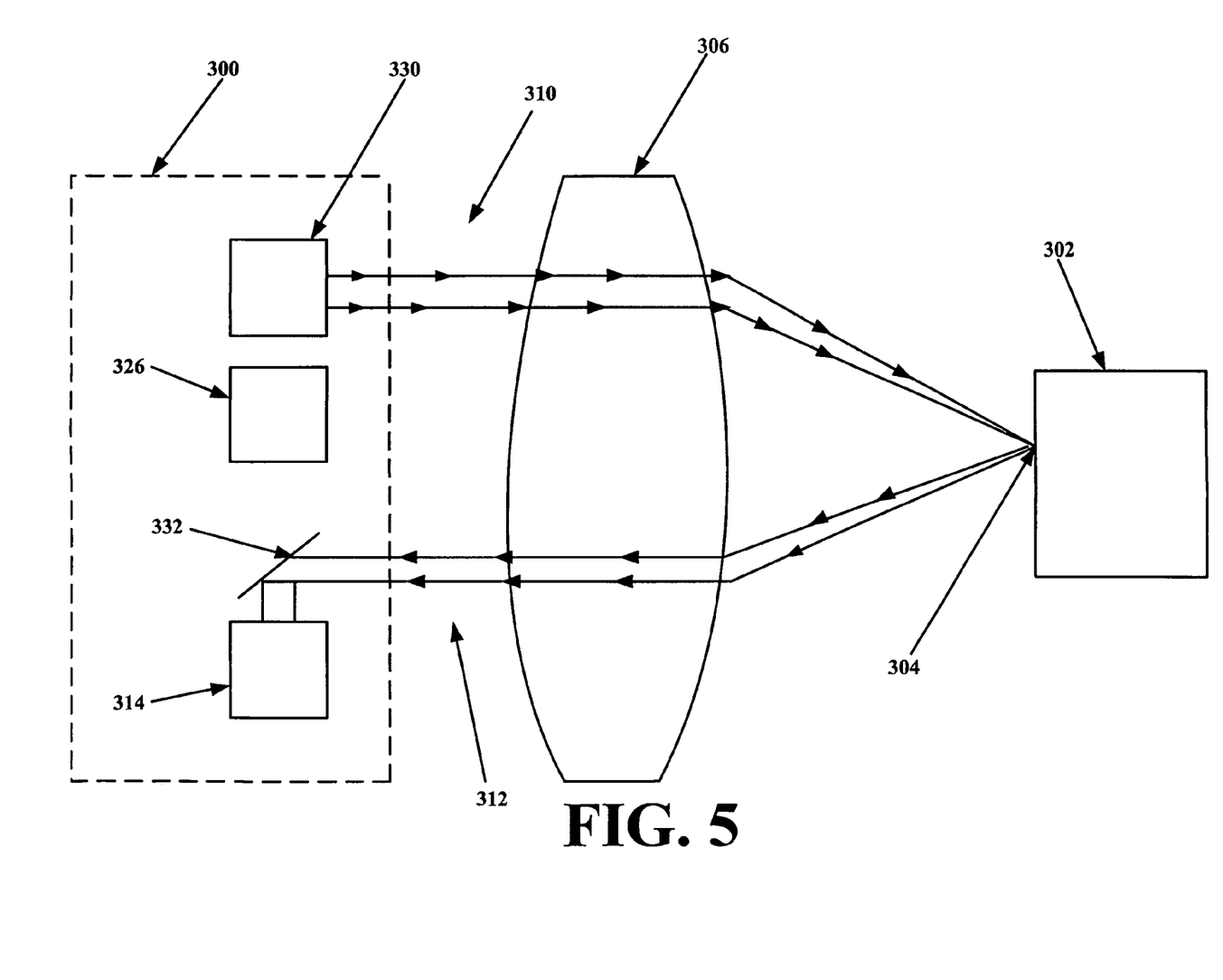
FIG. 5 is a block diagram of a sensor, in accordance with a third exemplary embodiment of the invention.

FIG. 5 is a block diagram of a sensor 300 in accordance with the third exemplary embodiment of the invention. The sensor 300 provides analysis of an object 302 at a focal point 304 of a lens 306. The sensor 300 includes a radiant energy source 330 directed at the lens 306. The radiant energy source 330 is capable of transmitting a first beam 310 of energy to the lens 306. The first beam 310 generated by the radiant energy source 330 is of sufficient intensity to vaporize a portion of the object 302 at the focal point 304 of the lens 306. A second beam 312 of energy is emitted from the vaporized portion of the object 302 and refracted through the lens 306 following a retro-reflective path respective to the first beam 310. A spectrometer 314 is positioned to receive, by way of a mirror 332, the second beam 312 of energy refracted from the lens 306. A path of the second beam 312 of energy is at least partially anti-parallel to a path of the first beam 310 of energy.

The radiant energy source 330 in the third exemplary embodiment is also capable of transmitting a first search beam (not shown, although a path of the first search beam is similar to a path shown for the first beam 310) prior to transmission of the first beam 310. The energy transmitted from the radiant energy source 330 to form the first search beam is not of sufficient intensity to vaporize an object, even after focusing by the lens 306. The first search beam, depending on the characteristics of the object 302, is retro-reflected back toward the lens 306 as a second search beam (not shown, although a path of the second search beam is similar to a path shown for the second beam 312 from the object 302 to the mirror 332). The second search beam is refracted back through the lens 306, directing second search beam back toward the sensor 300. More precisely, the second search beam radiates along a path anti-parallel to a path of the first search beam and toward the mirror 332. The mirror 332 (positioned differently than as is shown in FIG. 5) reflects the second search beam towards a detector 326, which receives the second search beam. The detector 326 detects whether the retro-reflected second search beam is in excess of a preselected radiant flux density level, which would indicate the presence of an optical device. An alternative to the mirror 332 in this embodiment would be to provide a single device in the position of the mirror 332 capable of performing the tasks of both the spectrometer 314 and the detector 326.

Figure 6:
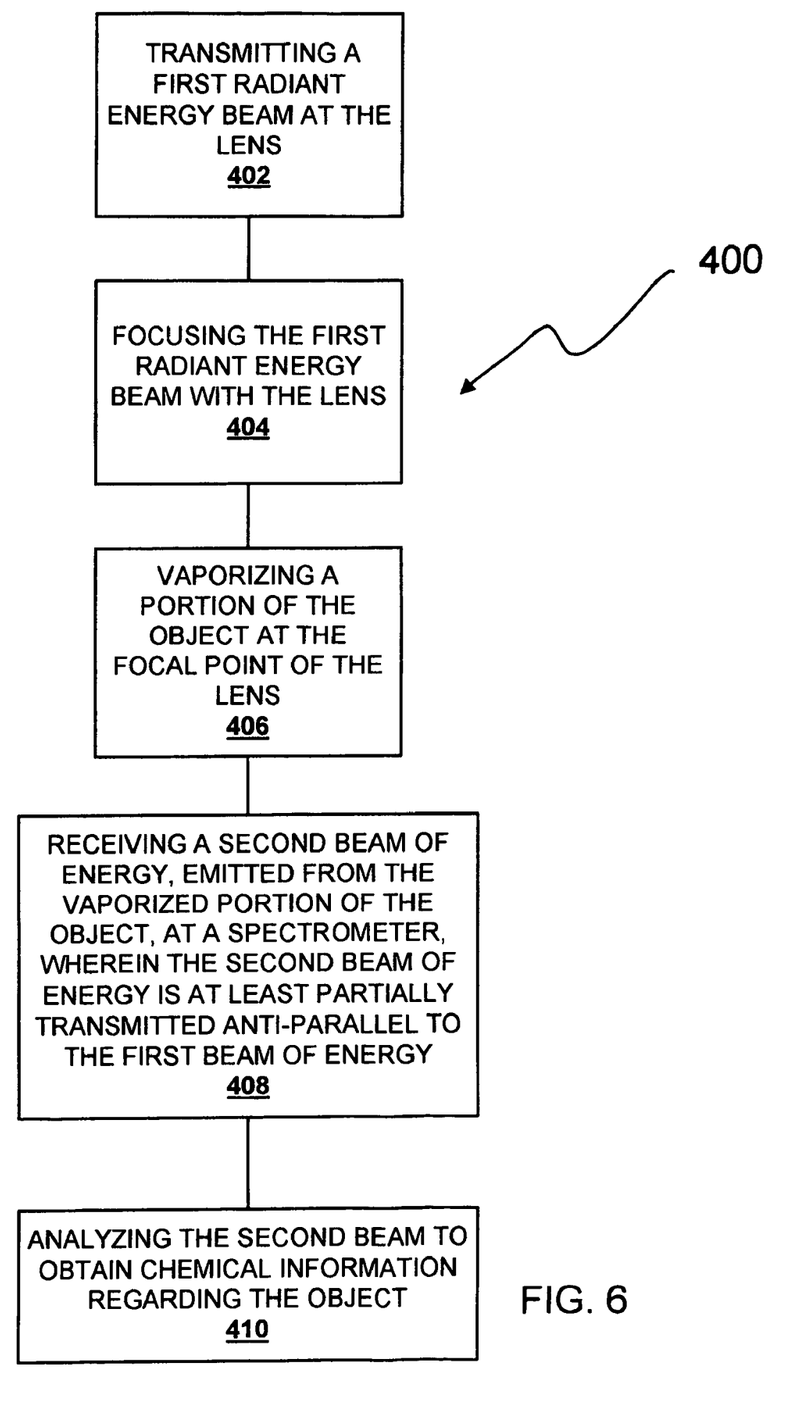
FIG. 6 is a flow chart illustrating a method of analyzing a remotely located object.

The flow chart of FIG. 6 shows the functionality and operation of a possible implementation of the method of analyzing a remotely located object, in accordance with the first exemplary embodiment shown in FIG. 3. In this regard, each block represents a module, segment, or step, which comprises one or more instructions for implementing the specified function. It should also be noted that in some alternative implementations, the functions noted in the blocks might occur out of the order noted in FIG. 6. For example, two blocks shown in succession in FIG. 6 may in fact be executed non-consecutively, substantially concurrently, or the blocks may sometimes be executed in the reverse order, depending upon the functionality involved, as will be further clarified herein.

Specifically, FIG. 6 is a flow chart 400 illustrating a method for analysis of a remotely located object 102 at a focal point 104 of a lens 106. The method 400 includes transmitting a first radiant energy beam 110 at the lens 106 (block 402).

The first radiant energy beam 110 is focused by the lens 106 (block 404). The focused first radiant energy beam 110 causes at least a portion of atoms of the object 102 at the focal point 104 to be vaporized (block 406). When vaporized, the atoms of the object 102 are raised to a high-energy state, which the vaporized atoms cannot maintain. Therefore, the vaporized atoms must decay from the high-energy state. The decay of the vaporized atoms involves an energy emission. The second beam 112 of energy is emitted from the decay of the vaporized atoms of the object 106 to a spectrometer 114. The second beam 112 of energy is at least partially transmitted anti-parallel to the first radiant energy beam 110 from the vaporized portion of the object to the spectrometer 114 (block 408).

The second beam 112 radiates toward the lens 106 and, is refracted toward the spectrometer 114. The spectrometer 114 is used to analyze the second beam 112 to obtain chemical information regarding the object 102 at the focal point 104 (block 410). Chemical analysis using a spectrometer is known to those having ordinary skill in the art.

Many applications exist for the sensor 100. One application involves identifying optical devices. If the lens 106 and object 102 are part of an optical device, the information retrieved through the spectrometer 114 may allow a user to verify that the object 102 is part of an optical device and even identify the optic device (as the identified material of the object 102 at the focal point 104 may be indicative of a particular optical device).

Another application may involve the remote identification of objects 102. If a lens 106 is transported to an object 102 such that the focal point 104 of the lens 106 coincides with the object 102, a remotely located focused radiant energy source 108 and spectrometer 114 may be used to identify the chemical nature of the object 102. The focused radiant energy source 108 and spectrometer 114, for this application, may, for instance, be located on an aerial vehicle or on a satellite with the targeting capability necessary to transmit the first radiant energy beam 110 through the lens 106. Other applications will be known to those having ordinary skill in the art.

Figure 7:
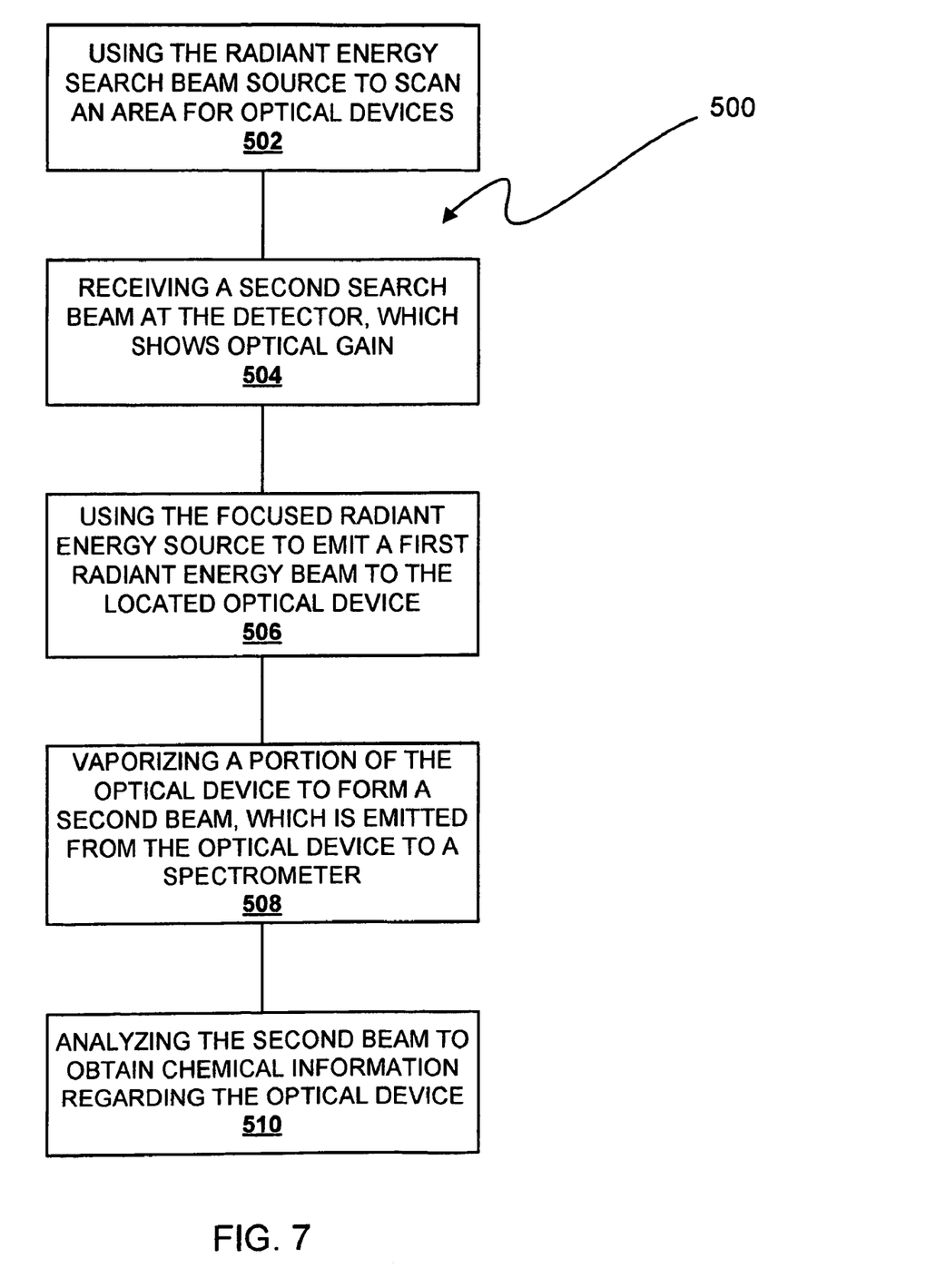
FIG. 7 is a flow chart illustrating a method of analyzing a remotely located object.

FIG. 7 is a flow chart illustrating the functionality and operation of a possible implementation of a method 500 of analyzing a remotely located object, in accordance with the second exemplary embodiment of the invention as shown in FIG. 4. Using the sensor 200 described in the second exemplary embodiment, a person may use the radiant energy search beam source 220 to scan an area for optical devices (block 502). The radiant energy search beam source 220 emits a first search beam 222 in various directions relative to a position of the sensor 200. If a second search beam 224 is received at the detector 226 and the detector 226 shows sufficient optical gain (resulting, in part, from the focusing of radiation), an optical device 202 has been located (block 504). The focused radiant energy source 208 may then be used to emit a first radiant energy beam 210 to the located optical device 204 (block 506). The emitted first radiant energy beam 210 vaporizes a portion of the optical device 202. That vaporization emits a second beam 212, from the optical device 202 to a spectrometer 214 (block 508). The spectrometer 214 is then used to analyze the second beam 212 to obtain chemical information regarding the optical device 204 (block 510).

It should be emphasized that the above-described embodiments of the present invention are merely possible examples of implementations, simply set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

I claim:

1. A sensor for analyzing an object at a focal point of a lens, the sensor comprising:
   a focused radiant energy source directed at the lens capable of generating a first beam of energy wherein the first beam is of sufficient intensity, when focused by the lens, to vaporize at least a portion of the object;
   a spectrometer positioned to receive a second beam of energy emitted from the object, wherein the second beam of energy is at least partially transmitted anti-parallel to the first beam of energy and wherein the second beam of energy comprises a spectral emission from a vaporized portion of the object;
   a radiant energy search beam source; and
   a detector for detecting a retro-reflected search beam which is in excess of a preselected radiant flux density level thereby indicating the presence of the object.

2. The sensor of claim 1, further comprising logic configured to determine whether the spectral emission has a focus optical gain.

3. The sensor of claim 1, further comprising logic configured to compare the spectral emission of the second beam to spectral emission properties of different materials, thereby analyzing the object.

4. The sensor of claim 1 further comprising a mirror positionable to direct the retro-reflected search beam to the detector and to direct the second beam to the spectrometer.

5. The sensor of claim 1 wherein the radiant energy search beam source and the focused radiant energy source are one combined radiant energy source.

6. The sensor of claim 5 wherein the combined radiant energy source is a laser.

7. The sensor of claim 1 wherein the spectrometer is a slitless spectrometer.

8. The sensor of claim 1 further comprising a memory device on which is stored spectral emission properties of different materials.

9. The sensor of claim 1 wherein the object is a tracking optical device.

10. A method of analyzing an object at a focal point of a lens, the method comprising the steps of:
    transmitting a first radiant energy beam at the lens;
    focusing the first radiant energy beam with the lens;
    vaporizing a portion of the object at the focal point of the lens;
    receiving a second beam of energy, emitted from the vaporized portion of the object, at a spectrometer, wherein the second beam of energy is at least partially transmitted anti-parallel to the first beam of energy;
    radiating an energy search beam at the lens; and
    detecting a retro-reflected search beam which is in excess of a preselected radiant flux density level thereby indicating the presence of the object.

11. The method of claim 10, further comprising the step of comparing a spectral emission of the second beam to spectral emission properties of different materials, thereby analyzing the object.

12. The method of claim 10 further comprising the step of directing the first radiant energy beam at a location from which a retro-reflected search beam was detected thereby analyzing the detected object.

13. The method of claim 10 further comprising the step of scanning the energy search beam over a region to locate the lens.

14. The method of claim 10 wherein the step of vaporizing vaporizes a relatively small portion of the object whereby operability of the object is unaffected.

15. The method of claim 10 further comprising the step of identifying a tracking optical device.

* * * * *